United States Patent
Collinson et al.

(10) Patent No.: US 10,695,226 B2
(45) Date of Patent: Jun. 30, 2020

(54) WOUND DRESSING AND METHOD OF TREATMENT

(71) Applicant: Smith & Nephew PLC, Watford, Hertfordshire (GB)

(72) Inventors: Sarah Jenny Collinson, Hull (GB); Philip Gowans, York (GB); Edward Yerbury Hartwell, Hull (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 452 days.

(21) Appl. No.: 14/209,907

(22) Filed: Mar. 13, 2014

(65) Prior Publication Data
US 2014/0316359 A1    Oct. 23, 2014

Related U.S. Application Data

(60) Provisional application No. 61/800,040, filed on Mar. 15, 2013.

(51) Int. Cl.
*A61M 1/00* (2006.01)
*A61F 13/00* (2006.01)
(Continued)

(52) U.S. Cl.
CPC .... *A61F 13/00068* (2013.01); *A61F 13/0209* (2013.01)

(58) Field of Classification Search
CPC ......... A61M 1/00; A61M 27/00; A61F 13/00; A61F 13/02; A61K 9/22
See application file for complete search history.

(56) References Cited

U.S. PATENT DOCUMENTS 2,331,271 A * 10/1943 Gilchrist ............. A61F 13/5323
604/368
3,972,328 A   8/1976 Chen
(Continued)

FOREIGN PATENT DOCUMENTS

DE    34 43 101       5/1986
EP    0 340 018      11/1989
(Continued)

OTHER PUBLICATIONS

International Search Report and Written Opinion, re PCT Application No. PCT/GB2014/050781, dated Jun. 13, 2014.
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

Embodiments disclosed herein are directed to negative pressure treatment systems and wound dressing systems, apparatuses, and methods that may be used for the treatment of wounds. In particular, some embodiments are directed to improved wound dressings comprising a bridge portion connecting two or more portions of an absorbent layer that facilitates trimming of the wound dressing to suitable sizes. Some embodiments provide for trimming the dressing in a gap between two or more portions of an absorbent layer and sealing the exposed portion of dressing after trimming when the dressing is applied to skin surrounding a wound.

28 Claims, 13 Drawing Sheets

(51) Int. Cl.
*A61F 13/02* (2006.01)
*A61M 27/00* (2006.01)
*A61K 9/22* (2006.01)

(56) References Cited

U.S. PATENT DOCUMENTS

| | | | |
|---|---|---|---|
| 4,029,598 A | 6/1977 | Neisius et al. | |
| 4,728,499 A | 3/1988 | Fehder | |
| 4,813,942 A | 3/1989 | Alvarez | |
| 4,886,697 A * | 12/1989 | Perdelwitz, Jr. | A47C 27/005 428/192 |
| 5,056,510 A | 10/1991 | Gilman | |
| 5,181,905 A | 1/1993 | Flam | |
| 5,238,732 A | 8/1993 | Krishnan | |
| 5,549,584 A | 8/1996 | Gross | |
| 5,707,499 A | 1/1998 | Joshi et al. | |
| 5,759,570 A | 6/1998 | Arnold | |
| 5,852,126 A | 12/1998 | Barnard et al. | |
| 6,071,267 A | 6/2000 | Zamierowski | |
| 6,626,891 B2 | 9/2003 | Ohmstede | |
| 6,685,681 B2 | 2/2004 | Lockwood et al. | |
| 6,752,794 B2 | 6/2004 | Lockwood et al. | |
| 6,776,769 B2 | 8/2004 | Smith | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,070,584 B2 | 7/2006 | Johnson et al. | |
| 7,108,683 B2 | 9/2006 | Zamierowski | |
| 7,216,651 B2 | 5/2007 | Argenta et al. | |
| 7,267,681 B2 * | 9/2007 | Dunshee | A61B 17/085 602/54 |
| 7,361,184 B2 | 4/2008 | Joshi | |
| 7,381,859 B2 | 6/2008 | Hunt et al. | |
| 7,429,689 B2 * | 9/2008 | Chen | A61F 13/4751 428/131 |
| 7,524,315 B2 | 4/2009 | Blott et al. | |
| 7,534,927 B2 | 5/2009 | Lockwood | |
| 7,569,742 B2 | 8/2009 | Haggstrom et al. | |
| 7,605,298 B2 | 10/2009 | Bechert et al. | |
| 7,611,500 B1 | 11/2009 | Lina et al. | |
| 7,615,036 B2 | 11/2009 | Joshi et al. | |
| 7,622,629 B2 | 11/2009 | Aail | |
| 7,625,362 B2 | 12/2009 | Boehringer et al. | |
| 7,699,823 B2 | 4/2010 | Haggstrom et al. | |
| 7,700,819 B2 | 4/2010 | Ambrosio et al. | |
| 7,708,724 B2 | 5/2010 | Weston | |
| 7,718,249 B2 | 5/2010 | Russell et al. | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,779,625 B2 | 8/2010 | Joshi et al. | |
| 7,811,269 B2 | 10/2010 | Boynton et al. | |
| 7,838,717 B2 | 11/2010 | Haggstrom et al. | |
| 7,846,141 B2 | 12/2010 | Weston | |
| 7,910,791 B2 | 3/2011 | Coffey | |
| 7,922,703 B2 | 4/2011 | Riesinger | |
| 7,959,624 B2 | 6/2011 | Riesinger | |
| 7,964,766 B2 | 6/2011 | Blott et al. | |
| 7,976,519 B2 | 7/2011 | Bubb et al. | |
| 8,034,037 B2 | 10/2011 | Adams et al. | |
| 8,062,272 B2 | 11/2011 | Weston | |
| 8,062,331 B2 | 11/2011 | Zamierowski | |
| 8,080,702 B2 | 12/2011 | Blott et al. | |
| 8,118,794 B2 | 2/2012 | Weston et al. | |
| 8,129,580 B2 | 3/2012 | Wilkes et al. | |
| 8,152,785 B2 | 4/2012 | Vitaris | |
| 8,162,907 B2 | 4/2012 | Heagle | |
| 8,192,409 B2 | 6/2012 | Hardman et al. | |
| 8,207,392 B2 | 6/2012 | Haggstrom et al. | |
| 8,235,972 B2 | 8/2012 | Adahan | |
| 8,241,261 B2 | 8/2012 | Randolph et al. | |
| 8,282,611 B2 | 10/2012 | Weston | |
| 8,303,552 B2 | 11/2012 | Weston | |
| 8,372,049 B2 | 2/2013 | Jaeb et al. | |
| 8,372,050 B2 | 2/2013 | Jaeb et al. | |
| 8,382,731 B2 | 2/2013 | Johannison | |
| 8,425,478 B2 | 4/2013 | Olson | |
| 8,444,612 B2 | 5/2013 | Patel et al. | |
| 8,454,580 B2 | 6/2013 | Locke et al. | |
| 8,460,255 B2 | 6/2013 | Joshi et al. | |
| 8,535,296 B2 | 9/2013 | Blott et al. | |
| 8,540,688 B2 | 9/2013 | Eckstein et al. | |
| 8,545,466 B2 | 10/2013 | Andresen et al. | |
| 8,568,386 B2 | 10/2013 | Malhi | |
| 8,628,505 B2 | 1/2014 | Weston | |
| 8,641,691 B2 | 2/2014 | Fink | |
| 8,663,198 B2 | 3/2014 | Buan et al. | |
| 8,715,256 B2 | 5/2014 | Greener | |
| 8,764,732 B2 * | 7/2014 | Hartwell | A61F 13/02 604/317 |
| 8,791,316 B2 | 7/2014 | Greener | |
| 8,795,243 B2 | 8/2014 | Weston | |
| 8,795,800 B2 | 8/2014 | Evans | |
| 8,801,685 B2 * | 8/2014 | Armstrong | A61F 13/02 604/319 |
| 8,808,274 B2 | 8/2014 | Hartwell | |
| 8,829,263 B2 | 9/2014 | Haggstrom et al. | |
| 8,834,451 B2 | 9/2014 | Blott et al. | |
| 8,834,452 B2 | 9/2014 | Hudspeth et al. | |
| 8,843,327 B2 | 9/2014 | Vernon-Harcourt et al. | |
| 8,916,742 B2 | 12/2014 | Smith | |
| 8,956,336 B2 | 2/2015 | Haggstrom et al. | |
| 9,012,714 B2 | 4/2015 | Fleischmann | |
| 9,061,095 B2 | 6/2015 | Adie et al. | |
| 9,067,003 B2 | 6/2015 | Buan et al. | |
| 9,127,665 B2 | 9/2015 | Locke et al. | |
| 9,168,330 B2 | 10/2015 | Joshi et al. | |
| 9,220,822 B2 | 12/2015 | Hartwell et al. | |
| 9,254,353 B2 | 2/2016 | Locke et al. | |
| 9,283,118 B2 | 3/2016 | Locke et al. | |
| 9,302,033 B2 | 4/2016 | Riesinger | |
| 9,375,353 B2 | 6/2016 | Vitaris et al. | |
| 9,375,521 B2 | 6/2016 | Hudspeth et al. | |
| 9,381,283 B2 | 7/2016 | Adams et al. | |
| 9,427,505 B2 | 8/2016 | Askem et al. | |
| 9,446,178 B2 | 9/2016 | Blott et al. | |
| 9,452,248 B2 | 9/2016 | Blott et al. | |
| 9,474,661 B2 | 10/2016 | Fouillet et al. | |
| 9,629,986 B2 | 4/2017 | Patel et al. | |
| 9,808,561 B2 | 11/2017 | Adie et al. | |
| 9,962,474 B2 | 5/2018 | Greener | |
| 2003/0125646 A1 | 7/2003 | Whitlock | |
| 2004/0057855 A1 | 3/2004 | Gerlach et al. | |
| 2006/0009744 A1 | 1/2006 | Edrman et al. | |
| 2007/0040454 A1 | 2/2007 | Freudenberger et al. | |
| 2007/0055209 A1 | 3/2007 | Patel et al. | |
| 2007/0225663 A1 | 9/2007 | Watt et al. | |
| 2008/0031748 A1 | 2/2008 | Ihle et al. | |
| 2008/0132821 A1 | 6/2008 | Propp et al. | |
| 2008/0306456 A1 | 12/2008 | Riesinger | |
| 2009/0125004 A1 | 5/2009 | Shen et al. | |
| 2009/0157024 A1 | 6/2009 | Song | |
| 2009/0234306 A1 | 9/2009 | Vitaris | |
| 2009/0234309 A1 * | 9/2009 | Vitaris | A61M 1/0049 604/313 |
| 2009/0299251 A1 | 12/2009 | Buan | |
| 2009/0299306 A1 | 12/2009 | Buan | |
| 2010/0125258 A1 | 5/2010 | Coulthard et al. | |
| 2010/0174250 A1 | 7/2010 | Hu et al. | |
| 2010/0259406 A1 | 10/2010 | Caso et al. | |
| 2010/0305526 A1 | 12/2010 | Robinson et al. | |
| 2010/0318052 A1 | 12/2010 | Ha et al. | |
| 2011/0004172 A1 | 1/2011 | Eckstein et al. | |
| 2011/0112492 A1 | 5/2011 | Bharti et al. | |
| 2011/0118683 A1 | 5/2011 | Weston | |
| 2011/0224631 A1 | 9/2011 | Simmons | |
| 2011/0257611 A1 | 10/2011 | Locke et al. | |
| 2011/0282309 A1 | 11/2011 | Adie | |
| 2011/0313374 A1 | 12/2011 | Lockwood et al. | |
| 2012/0051945 A1 | 3/2012 | Orndorff et al. | |
| 2012/0095380 A1 | 4/2012 | Gergley et al. | |

(56) References Cited

U.S. PATENT DOCUMENTS

| | | | |
|---|---|---|---|
| 2012/0116334 A1 | 5/2012 | Albert | |
| 2012/0123358 A1 | 5/2012 | Hall et al. | |
| 2012/0136326 A1 | 5/2012 | Croizat et al. | |
| 2012/0150078 A1 | 6/2012 | Chen et al. | |
| 2012/0222687 A1 | 9/2012 | Czajka, Jr. et al. | |
| 2012/0232502 A1 | 9/2012 | Lowing | |
| 2013/0066285 A1 | 3/2013 | Locke et al. | |
| 2013/0066289 A1 | 3/2013 | Song et al. | |
| 2013/0090616 A1 | 4/2013 | Neubauer | |
| 2013/0138054 A1 | 5/2013 | Fleischmann | |
| 2013/0144227 A1 | 6/2013 | Locke et al. | |
| 2013/0144230 A1 | 6/2013 | Wu et al. | |
| 2013/0150814 A1 | 6/2013 | Buan | |
| 2013/0165878 A1 | 6/2013 | Heagle | |
| 2013/0274688 A1 | 10/2013 | Weston | |
| 2013/0296762 A1 | 11/2013 | Toth | |
| 2013/0302545 A1 | 11/2013 | Schnelker et al. | |
| 2013/0310781 A1 | 11/2013 | Phillips et al. | |
| 2014/0010673 A1 | 1/2014 | Locke et al. | |
| 2014/0012213 A1 | 1/2014 | Locke et al. | |
| 2014/0114268 A1 | 4/2014 | Auguste et al. | |
| 2014/0127148 A1 | 5/2014 | Derain | |
| 2014/0171888 A1 | 6/2014 | Croizat et al. | |
| 2014/0200533 A1 | 7/2014 | Whyte et al. | |
| 2014/0228791 A1 | 8/2014 | Hartwell | |
| 2014/0303575 A1 | 10/2014 | May | |
| 2014/0350496 A1 | 11/2014 | Riesinger | |
| 2015/0032035 A1 | 1/2015 | Banwell et al. | |
| 2015/0057625 A1 | 2/2015 | Coulthard et al. | |
| 2015/0065965 A1 | 3/2015 | Haggstrom et al. | |
| 2015/0119831 A1 | 4/2015 | Robinson et al. | |
| 2015/0159066 A1 | 6/2015 | Hartwell et al. | |
| 2015/0174304 A1 | 6/2015 | Askem et al. | |
| 2015/0182677 A1 | 7/2015 | Collinson et al. | |
| 2015/0190286 A1 | 7/2015 | Allen et al. | |
| 2015/0216733 A1 | 8/2015 | Allen et al. | |
| 2015/0306273 A1 | 10/2015 | Karim et al. | |
| 2015/0308994 A1 | 10/2015 | Hammond et al. | |
| 2015/0335798 A1 | 11/2015 | De Samber et al. | |
| 2016/0000610 A1 | 1/2016 | Riesinger | |
| 2016/0000611 A1 | 1/2016 | Niederauer et al. | |
| 2016/0081859 A1 | 3/2016 | Hartwell | |
| 2016/0136339 A1 | 5/2016 | Begin et al. | |
| 2016/0144084 A1 | 5/2016 | Collinson et al. | |
| 2016/0262942 A1 | 9/2016 | Riesinger | |
| 2016/0298620 A1 | 10/2016 | Cordoba et al. | |
| 2016/0317357 A1 | 11/2016 | Vitaris et al. | |
| 2017/0128642 A1 | 5/2017 | Buan | |

FOREIGN PATENT DOCUMENTS

| | | |
|---|---|---|
| EP | 1 955 887 | 8/2008 |
| EP | 2 366 721 | 9/2011 |
| EP | 2 529 767 | 12/2012 |
| EP | 2 477 674 | 7/2013 |
| FR | 1163907 | 10/1958 |
| GB | 1255395 | 12/1971 |
| GB | 2389794 | 12/2003 |
| JP | 2011-521736 | 7/2011 |
| WO | WO 1983/00742 | 3/1983 |
| WO | WO 2004/077387 | 9/2004 |
| WO | WO 2008/039223 | 4/2008 |
| WO | WO 2011/112870 | 9/2011 |
| WO | WO 2011/115908 | 9/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/069793 | 5/2012 |
| WO | WO 2012/069794 | 5/2012 |
| WO | WO 2012/143665 | 10/2012 |
| WO | WO 2013/029652 | 3/2013 |
| WO | WO 2013/064852 | 5/2013 |
| WO | WO 2013/076450 | 5/2013 |
| WO | WO 2013/110008 | 7/2013 |
| WO | WO 2013/136181 | 11/2013 |
| WO | WO 2014/020440 | 2/2014 |
| WO | WO 2014/020443 | 2/2014 |
| WO | WO 2014/140606 | 9/2014 |
| WO | WO 2014/140608 | 9/2014 |
| WO | WO 2015/022340 | 2/2015 |

OTHER PUBLICATIONS

International Search Report and Written Opinion, re PCT Application No. PCT/GB2014/050786, dated Jun. 12, 2014.
Kendall ULTEC Hydrocolloid Dressing (4"×4"), product ordering page, web page downloaded Jul. 13, 2014.
Protz, Kerstin: "Modern Wundauflagen unterstutzen Heilungsprozess", Wundversorgung: Indikation and Anwendung, Geriatrie Journal, Apr. 2005, pp. 3333-3339, with translation.
Membrane Filters, in 17 pages, from website: http://www.advantecmfs.com/catalog/filt/membrane.pdf#page=11 (date unknown, but believed to be copyright 2001-2011).
Smith & Nephew, "PICO Single Use Negative Pressure Wound Therapy System", spiral booklet, Mar. 2011, in 7 pages.
U.S. Appl. No. 15/536,271, filed Jun. 15, 2017, Askem et al.
U.S. Appl. No. 15/536,305, filed Jun. 15, 2017, Askem et al.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

* cited by examiner

WOUND DRESSING AND METHOD OF TREATMENT

INCORPORATION BY REFERENCE

The present application claims the benefit under 35 U.S.C. § 119(e) of U.S. Provisional Patent Application No. 61/800,040, filed on Mar. 15, 2013, entitled "WOUND DRESSING AND METHOD OF TREATMENT," the entire contents of which is hereby incorporated by reference herein in its entirety and for all purposes. This embodiments disclosed in this application are related to U.S. Provisional Application Ser. No. 61/785,054, filed Mar. 14, 2013, titled "WOUND DRESSING AND METHOD OF TREATMENT," and U.S. Patent Publication No. 2011/0282309 A1, published Nov. 17, 2011, titled "WOUND DRESSING AND METHOD OF USE," the entireties of each of which are hereby incorporated by reference. Embodiments from the incorporated by reference applications may be interchanged and/or added to any of the embodiments disclosed herein.

FIELD OF THE INVENTION

Embodiments described herein relate to apparatuses, systems, and methods the treatment of wounds, for example using dressings in combination with negative pressure wound therapy.

SUMMARY OF THE INVENTION

Certain embodiments disclosed herein relate to improved wound dressings that exhibit enhanced adaptability. Such dressings may have advantages over prior art dressings which may be more difficult to apply, particularly around lengthy incision sites or irregularly shaped wounds. Also disclosed are improved methods of use and systems for use of the same, preferably in conjunction with negative pressure wound therapy.

In one embodiment, a wound treatment apparatus for treatment of a wound site comprises:
  a backing layer having an upper surface and a lower surface and defining a perimeter configured to be positioned over skin surrounding a wound site;
  a wound contact layer;
  an absorbent material positioned between the backing layer and the wound contact layer and comprising one or more bridging portions having a smaller width than adjacent portions of the absorbent material; and
  a port configured to transmit negative pressure through the backing layer for the application of topical negative pressure at the wound site.

In some embodiments, the port may comprise an opening in the backing layer. The port may comprise a port member attached to the backing layer over an opening in the backing layer. The port member may be sealed to the upper surface of the backing layer. Some embodiments may further comprise a transmission layer between the wound contact layer and the absorbent layer having a similar footprint to that of the absorbent material. Some embodiments may further comprise an acquisition distribution layer between the wound contact layer and the absorbent layer having a similar footprint to that of the absorbent material.

The absorbent layer may have a rectangular shape having a longitudinal axis extend along its length. The absorbent material may comprise one or more bridging portions centered on the longitudinal axis. The absorbent material may comprise three or more bridging portions centered on the longitudinal axis. The bridging one or more bridging portions may also be offset from the longitudinal axis. The one or more bridging portions may have a width that is less than ⅓ the width of adjacent portions of absorbent material. The one or more bridging portions may have a width that is less than ¼ the width of adjacent portions of absorbent material. The one or more bridging portions may have a width that is less than ⅛ the width of adjacent portions of absorbent material. The absorbent material may have a T-shape with a bridging portion on each leg of the T. The absorbent material may have a T-shape with at least one bridging portion on each leg of the T. The absorbent material may comprise a plurality of cells each separated by one or more bridging portions. The absorbent material may comprise a plurality of cells, and wherein each of the plurality of cells is connected to at least one adjacent cell by one or more bridging portions.

The wound treatment apparatus may be rolled into a tape which can be cut along the one or more bridging portions.

In another embodiment, a wound treatment apparatus for treatment of a wound site comprises:
  a backing layer having an upper surface and a lower surface and defining a perimeter configured to be positioned over skin surrounding a wound site;
  a wound contact layer;
  an absorbent material positioned between the backing layer and the wound contact layer; and
  a plurality of ports configured to transmit negative pressure spaced apart on the backing layer.

The wound treatment apparatus may be configured to be rolled into a tape. The plurality of ports each may comprise an opening in the backing layer covered with a releasable tab. The absorbent material may comprise one or more bridging portions having a smaller width than adjacent portions of the absorbent material. The plurality of ports are spaced apart lengthwise on the backing layer when the wound treatment apparatus is rolled into a tape.

Some embodiments may further comprise a fluidic connector configured to supply negative pressure to the port. Some embodiments may further comprise a source of negative pressure configured to supply negative pressure through the port. Some embodiments may further comprise adhesive strips configured to seal the backing layer to skin surrounding a wound after the apparatus is cut along the one or more bridging portions.

In another embodiment, a method of treating a wound comprises:
  providing a wound dressing comprising:
    a backing layer;
    a wound contact layer; and
    an absorbent material positioned between the backing layer and the wound contact layer, the absorbent material comprising one or more bridging portions having a smaller width than adjacent portions of the absorbent material;
  removing a portion of the wound dressing along at least one of the one or more bridging portions to create a main wound dressing portion with one or more exposed portions;
  positioning the main wound dressing portion over a wound;
  sealing the main wound dressing to skin surrounding the wound, wherein sealing comprises sealing the one or more exposed portions of the main wound dressing portion; and
  applying negative pressure to the wound through the backing layer of the main wound dressing portion.

In some embodiments of the method, removing a portion of the wound dressing comprises cutting the wound dressing across at least one of the one or more bridging portions. At least a portion of the wound dressing may comprise pre-cut score marks to facilitate removing of the portion of wound dressing. The dressing may comprise a plurality of openings in the backing layer covered with a releasable tab, and negative pressure may be applied to the backing layer through one of the openings. The dressing may comprise a plurality of openings in the backing layer covered with a releasable tab, and negative pressure may be applied to the backing layer through two or more of the openings.

The portions of the wound dressing may be removed to size the main wound dressing portion for positioning over an incisional wound. The portions of the wound dressing may be removed to size the main wound dressing portion for positioning over an elongate leg wound. The portions of the wound dressing may be removed to size the main wound dressing portion for positioning over an arcuate incisional wound.

A method of treating a wound, comprising:
  providing a wound dressing comprising a backing layer, a wound contact layer, an absorbent material positioned between the backing layer and the wound contact layer, and a plurality of spaced apart openings in the backing layer each covered with a releasable tab, the wound dressing configured into a roll;
  unrolling a portion of the wound dressing from the roll;
  removing a portion of the wound dressing from the roll, the removed portion comprising at least one opening in the backing layer covered with a releasable tab;
  positioning the removed portion of the wound dressing over a wound; and
  applying negative pressure through at least one opening in the backing layer after a releasable tab has been removed.

DETAILED DESCRIPTION OF THE PREFERRED EMBODIMENTS

Figure 1:
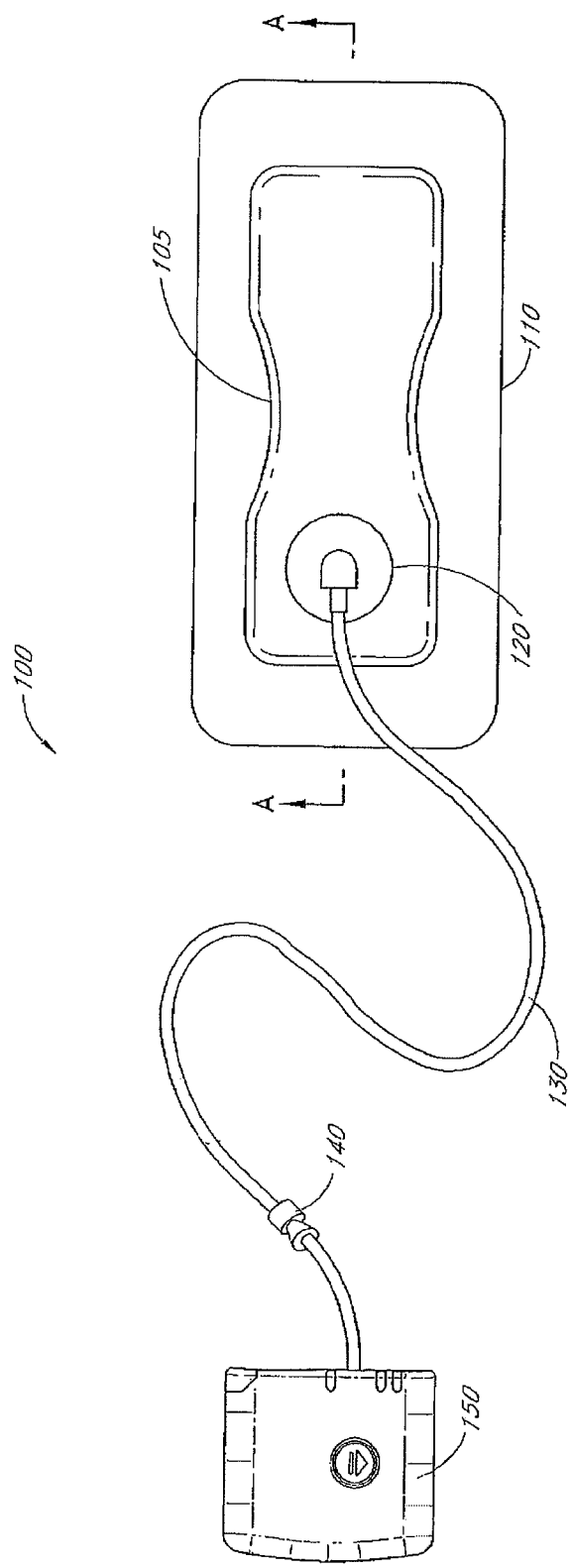
FIG. 1 illustrates an embodiment of a wound treatment system.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as $-X$ mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of $-X$ mmHg reflects absolute pressure that is $X$ mmHg below 760 mmHg or, in other words, an absolute pressure of $(760-X)$ mmHg. In addition, negative pressure that is "less" or "smaller" than $X$ mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg).

The negative pressure range for some embodiments of the present disclosure can be approximately $-80$ mmHg, or between about $-20$ mmHg and $-200$ mmHg. Note that these pressures are relative to normal ambient atmospheric pressure. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even 150 mmHg, can be supplied by the negative pressure apparatus. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

FIG. 1 illustrates an embodiment of a TNP wound treatment system 100 comprising a wound dressing 110 in combination with a pump 150. As stated above, the wound dressing 110 can be any wound dressing embodiment disclosed herein including without limitation dressing embodiment or have any combination of features of any number of wound dressing embodiments disclosed herein. Here, the dressing 110 may be placed over a wound as described previously, and a conduit 130 may then be connected to the port 120, although in some embodiments the dressing 101 may be provided with at least a portion of the conduit 130 preattached to the port 120. Preferably, the dressing 110 is provided as a single article with all wound dressing elements (including the port 120) pre-attached and integrated into a single unit. The wound dressing 110 may then be connected, via the conduit 130, to a source of negative pressure such as the pump 150. The pump 150 can be miniaturized and portable, although larger conventional pumps may also be used with the dressing 110. In some embodiments, the pump 150 may be attached or mounted onto or adjacent the dressing 110. A connector 140 may also be provided so as to permit the conduit 130 leading to the wound dressing 110 to be disconnected from the pump, which may be useful for example during dressing changes.

Figure 2A:
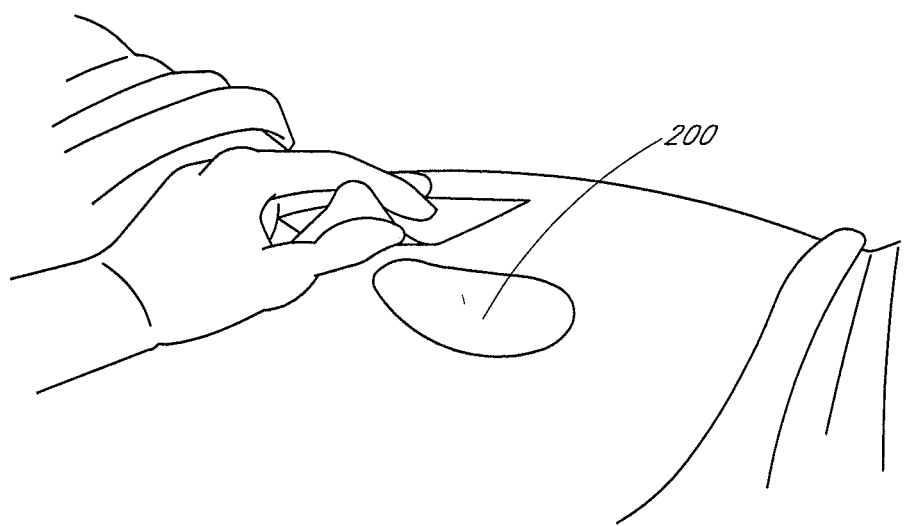
FIGS. 2A-D illustrate the use and application of an embodiment of a wound treatment system onto a patient.

FIGS. 2A-D illustrate the use of an embodiment of a TNP wound treatment system being used to treat a wound site on a patient. FIG. 2A shows a wound site 200 being cleaned and prepared for treatment. Here, the healthy skin surrounding the wound site 200 is preferably cleaned and excess hair removed or shaved. The wound site 200 may also be irrigated with sterile saline solution if necessary. Optionally, a skin protectant may be applied to the skin surrounding the wound site 200. If necessary, a wound packing material, such as foam or gauze, may be placed in the wound site 200. This may be preferable if the wound site 200 is a deeper wound.

Figure 2B:
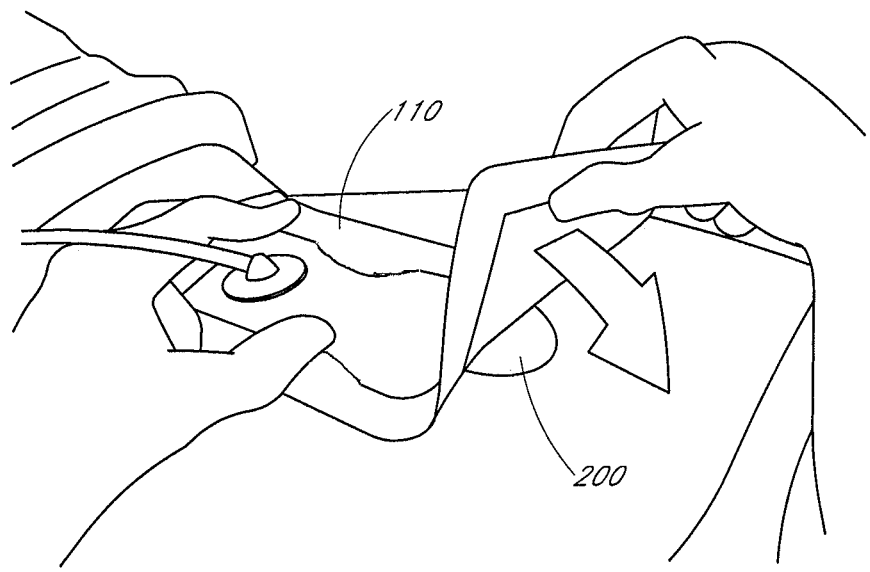

After the skin surrounding the wound site 200 is dry, and with reference now to FIG. 2B, the wound dressing 110 may be positioned and placed over the wound site 200. Preferably, the wound dressing 110 is placed with the wound contact layer 2102 over and/or in contact with the wound site 200. In some embodiments, an adhesive layer is provided on the lower surface 2101 of the wound contact layer 2102, which may in some cases be protected by an optional release layer to be removed prior to placement of the wound dressing 110 over the wound site 200. Preferably, the dressing 110 is positioned such that the port 2150 is in a raised position with respect to the remainder of the dressing 110 so as to avoid fluid pooling around the port. In some embodiments, the dressing 110 is positioned so that the port 2150 is not directly overlying the wound, and is level with or at a higher point than the wound. To help ensure adequate sealing for TNP, the edges of the dressing 110 are preferably smoothed over to avoid creases or folds.

Figure 2C:
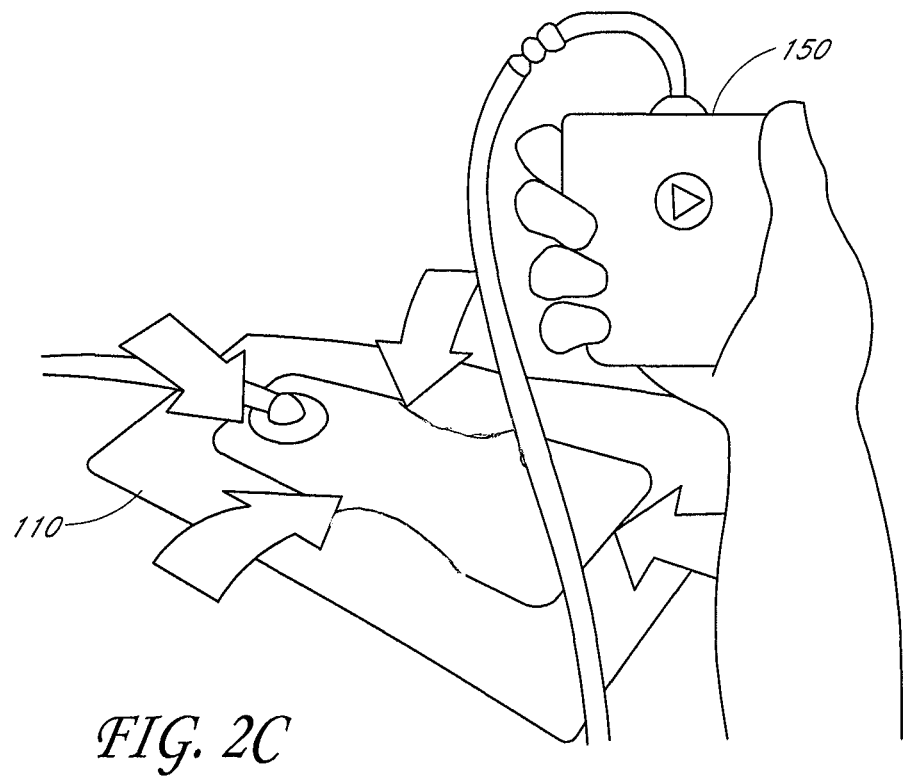

With reference now to FIG. 2C, the dressing 110 is connected to the pump 150. The pump 150 is configured to apply negative pressure to the wound site via the dressing 110, and typically through a conduit. In some embodiments, and as described above in FIG. 1, a connector may be used to join the conduit from the dressing 110 to the pump 150. Upon the application of negative pressure with the pump 150, the dressing 110 may, in some embodiments, partially collapse and present a wrinkled appearance as a result of the evacuation of some or all of the air underneath the dressing 110. In some embodiments, the pump 150 may be configured to detect if any leaks are present in the dressing 110, such as at the interface between the dressing 110 and the skin surrounding the wound site 200. Should a leak be found, such leak is preferably remedied prior to continuing treatment.

Figure 2D:
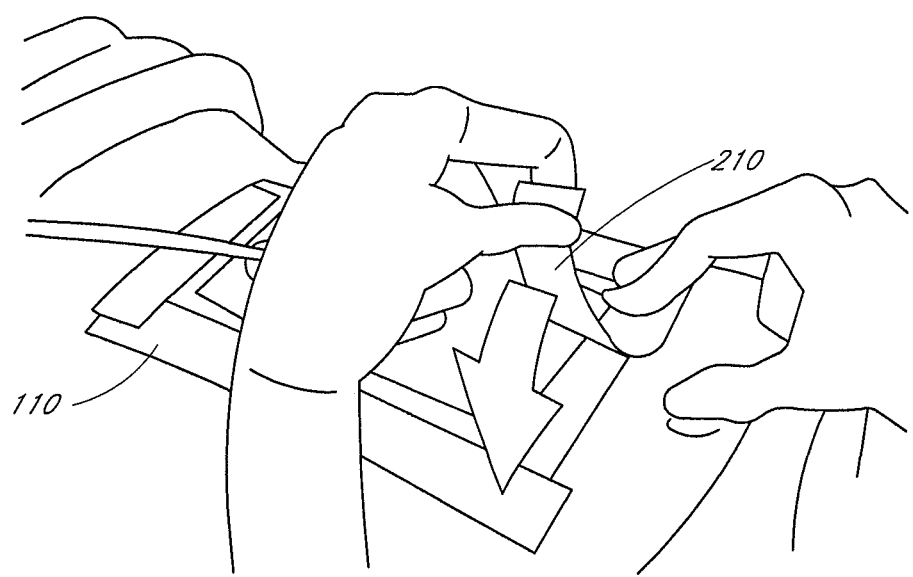

Turning to FIG. 2D, additional fixation strips 210 may also be attached around the edges of the dressing 110. Such fixation strips 210 may be advantageous in some situations so as to provide additional sealing against the skin of the patient surrounding the wound site 200. For example, the fixation strips 210 may provide additional sealing for when a patient is more mobile. In some cases, the fixation strips 210 may be used prior to activation of the pump 150, particularly if the dressing 110 is placed over a difficult to reach or contoured area.

Treatment of the wound site 200 preferably continues until the wound has reached a desired level of healing. In some embodiments, it may be desirable to replace the dressing 110 after a certain time period has elapsed, or if the dressing is full of wound fluids. During such changes, the pump 150 may be kept, with just the dressing 110 being changed.

Figure 3A:
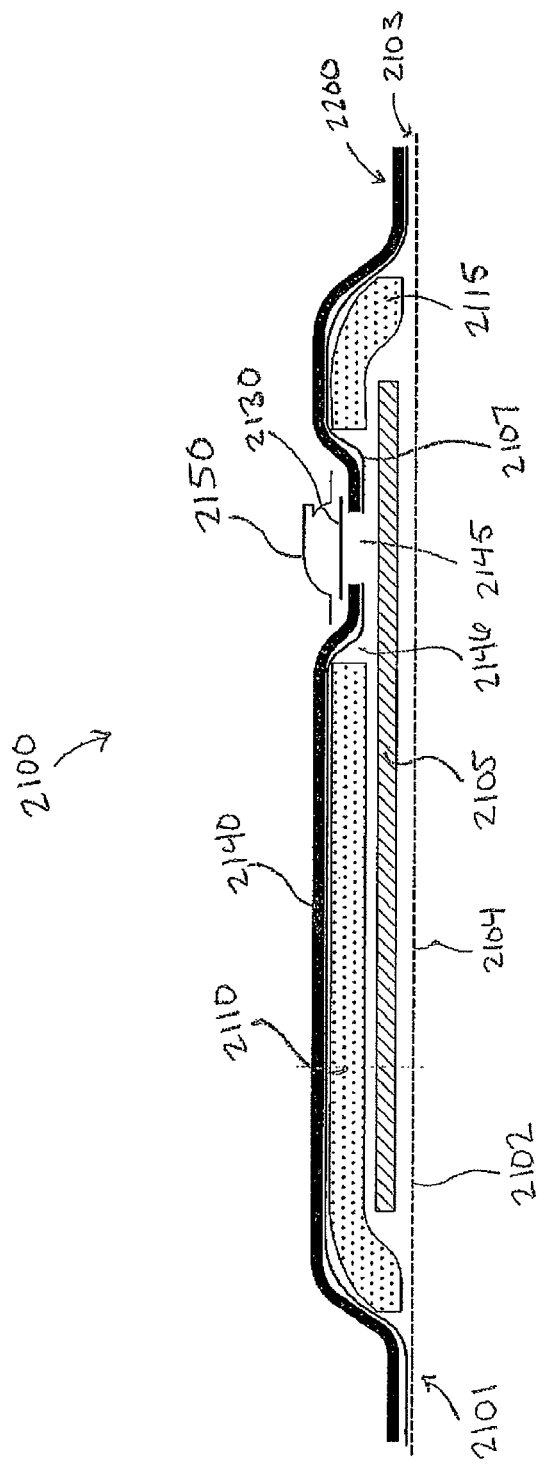
FIG. 3A illustrates an embodiment of a wound dressing in cross-section.
Figure 3B:
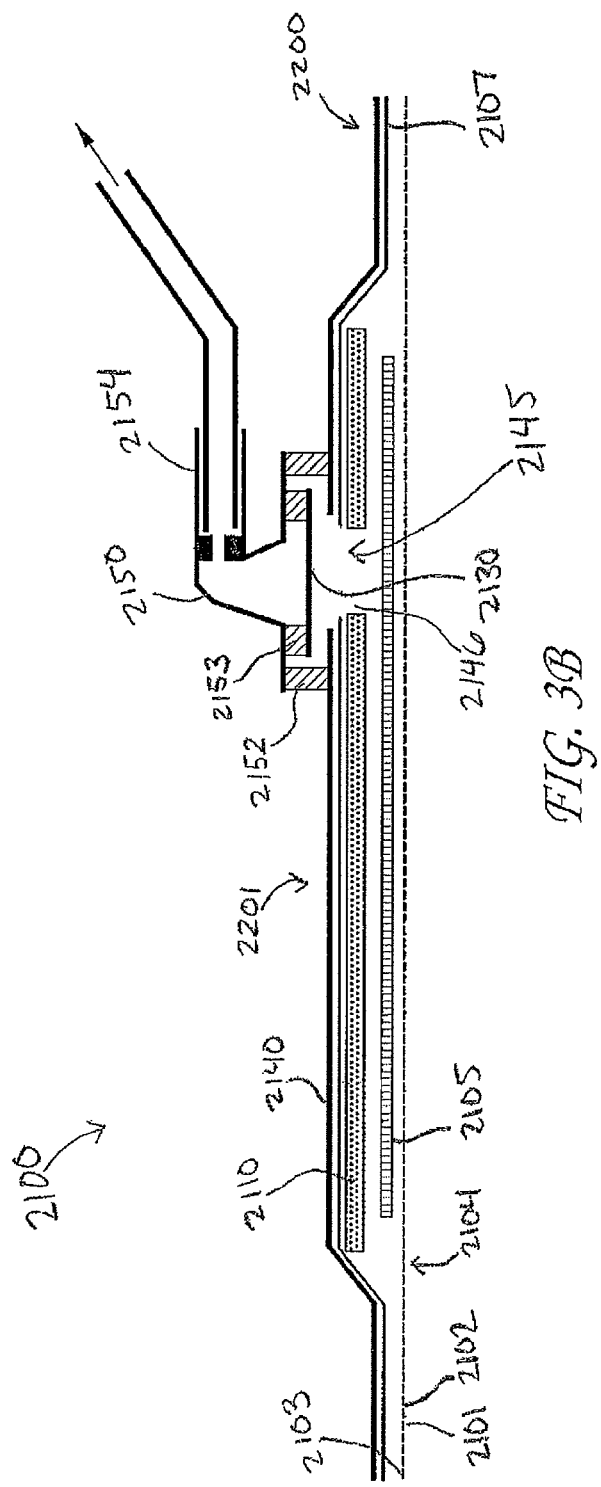
FIG. 3B illustrates another embodiment of a wound dressing in cross-section.
Figure 3C:
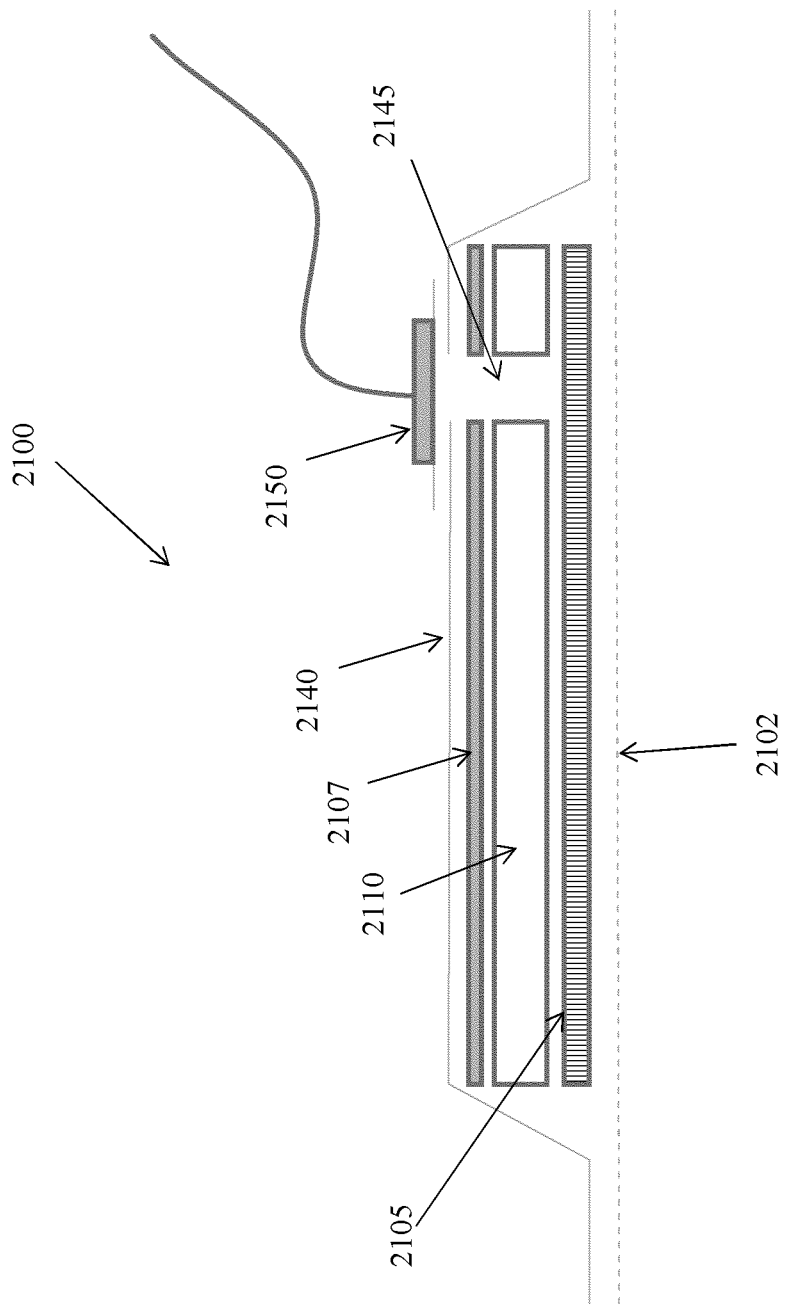
FIG. 3C illustrates another embodiment of a wound dressing in cross-section.

FIGS. 3A-C illustrate cross-sections through a wound dressing 2100 similar to the wound dressing of FIG. 1 according to an embodiment of the disclosure. A view from above the wound dressing 2100 is illustrated in FIG. 1 with the line A-A indicating the location of the cross-section shown in FIGS. 3A and 3B. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, both of which are described in greater detail below. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 2105 and an absorbent layer 2110.

As illustrated in FIGS. 3A-C, a lower surface 2101 of the wound dressing 2100 may be provided with an optional wound contact layer 2102. The wound contact layer 2102 can be a polyurethane layer or polyethylene layer or other flexible layer which is perforated, for example via a hot pin process, laser ablation process, ultrasound process or in some other way or otherwise made permeable to liquid and gas. The wound contact layer 2102 has a lower surface 2101 and an upper surface 2103. The perforations 2104 preferably comprise through holes in the wound contact layer 2102 which enable fluid to flow through the layer 2102. The wound contact layer 2102 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 2102 may help maintain the integrity of the entire dressing 2100 while also creating an air tight seal around the absorbent pad in order to maintain negative pressure at the wound.

Some embodiments of the wound contact layer 2102 may also act as a carrier for an optional lower and upper adhesive layer (not shown). For example, a lower pressure sensitive adhesive may be provided on the lower surface 2101 of the wound dressing 2100 whilst an upper pressure sensitive adhesive layer may be provided on the upper surface 2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 2100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure. The layer 2105 may be formed of a material having a three dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

With reference to FIGS. 3A-C, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Additionally, the obscuring layer 2107 can be positioned adjacent to the backing layer, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™11C-450. In some embodiments, the absorbent layer 2110 may comprise a composite comprising superabsorbent powder, fibrous material such as cellulose, and bonding fibers. In a preferred embodiment, the composite is an airlaid, thermally-bonded composite.

An orifice 2145 is preferably provided in the backing layer 2140 to allow a negative pressure to be applied to the dressing 2100. A suction port 2150 is preferably attached or sealed to the top of the backing layer 2140 over an orifice 2145 made into the dressing 2100, and communicates negative pressure through the orifice 2145. A length of tubing 2220 may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material, for example using the embodiments described below in FIGS. 23A-B.

Preferably the absorbent layer 2110 and the obscuring layer 2107 include at least one through hole 2146 located so as to underlie the port 2150. The through hole 2146, while illustrated here as being larger than the hole through the obscuring layer 2107 and backing layer 2140, may in some embodiments be bigger or smaller than either. Of course, the respective holes through these various layers 2107, 2140, and 2110 may be of different sizes with respect to each other. As illustrated in FIGS. 3A-C a single through hole can be used to produce an opening underlying the port 2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer 2100 is near saturation.

The aperture or through-hole 2146 is preferably provided in the absorbent layer 2110 and the obscuring layer 2107 beneath the orifice 2145 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2145 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane film and an adhesive pattern spread onto the film. The polyurethane film is preferably moisture vapor permeable and may be manufactured from a material that has an increased water transmission rate when wet.

The absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

As shown in FIG. 3A, one embodiment of the wound dressing 2100 comprises an aperture 2146 in the absorbent layer 2110 situated underneath the port 2150. In use, for example when negative pressure is applied to the dressing 2100, a wound facing portion of the port 150 may thus come into contact with the transmission layer 2105, which can thus aid in transmitting negative pressure to the wound site even when the absorbent layer 2110 is filled with wound fluids. Some embodiments may have the backing layer 2140 be at least partly adhered to the transmission layer 2105. In some embodiments, the aperture 2146 is at least 1-2 mm larger than the diameter of the wound facing portion of the port 2150, or the orifice 2145.

A filter element 2130 that is impermeable to liquids, but permeable to gases is provided to act as a liquid barrier, and to ensure that no liquids are able to escape from the wound dressing. The filter element may also function as a bacterial barrier. Typically the pore size is 0.2 µm. Suitable materials for the filter material of the filter element 2130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the backing layer 2140 over the orifice 2145. For example, the filter element 2130 may be molded into the port 2150, or may be adhered to both the top of the backing layer 2140 and bottom of the port 2150 using an adhesive such as, but not limited to, a UV cured adhesive.

In FIG. 3B, an embodiment of the wound dressing 2100 is illustrated which comprises spacer elements 2152, 2153 in conjunction with the port 2150 and the filter 2130. With the addition of such spacer elements 2152, 2153, the port 2150 and filter 2130 may be supported out of direct contact with the absorbent layer 2110 and/or the transmission layer 2105. The absorbent layer 2110 may also act as an additional spacer element to keep the filter 2130 from contacting the transmission layer 2105. Accordingly, with such a configuration contact of the filter 2130 with the transmission layer 2105 and wound fluids during use may thus be minimized. As contrasted with the embodiment illustrated in FIG. 3A, the aperture 2146 through the absorbent layer 2110 and the obscuring layer 2107 may not necessarily need to be as large or larger than the port 2150, and would thus only need to be large enough such that an air path can be maintained from the port to the transmission layer 2105 when the absorbent layer 2110 is saturated with wound fluids.

With reference now to FIG. 3C, which shares many of the elements illustrated in FIGS. 3A-C, the embodiment illustrated here comprises the backing layer 2140, masking layer 2107, and absorbent layer 2110, all of which have a cut or opening made therethrough which communicate directly to the transmission layer 2105 so as to form the orifice 2145. The suction port 2150 is preferably situated above it and communicates with the orifice 2145.

In particular for embodiments with a single port 2150 and through hole, it may be preferable for the port 2150 and through hole to be located in an off-center position as illustrated in FIGS. 3A-C and in FIG. 1. Such a location may permit the dressing 2100 to be positioned onto a patient such that the port 2150 is raised in relation to the remainder of the dressing 2100. So positioned, the port 2150 and the filter 2130 may be less likely to come into contact with wound fluids that could prematurely occlude the filter 2130 so as to impair the transmission of negative pressure to the wound site.

Figure 4A:
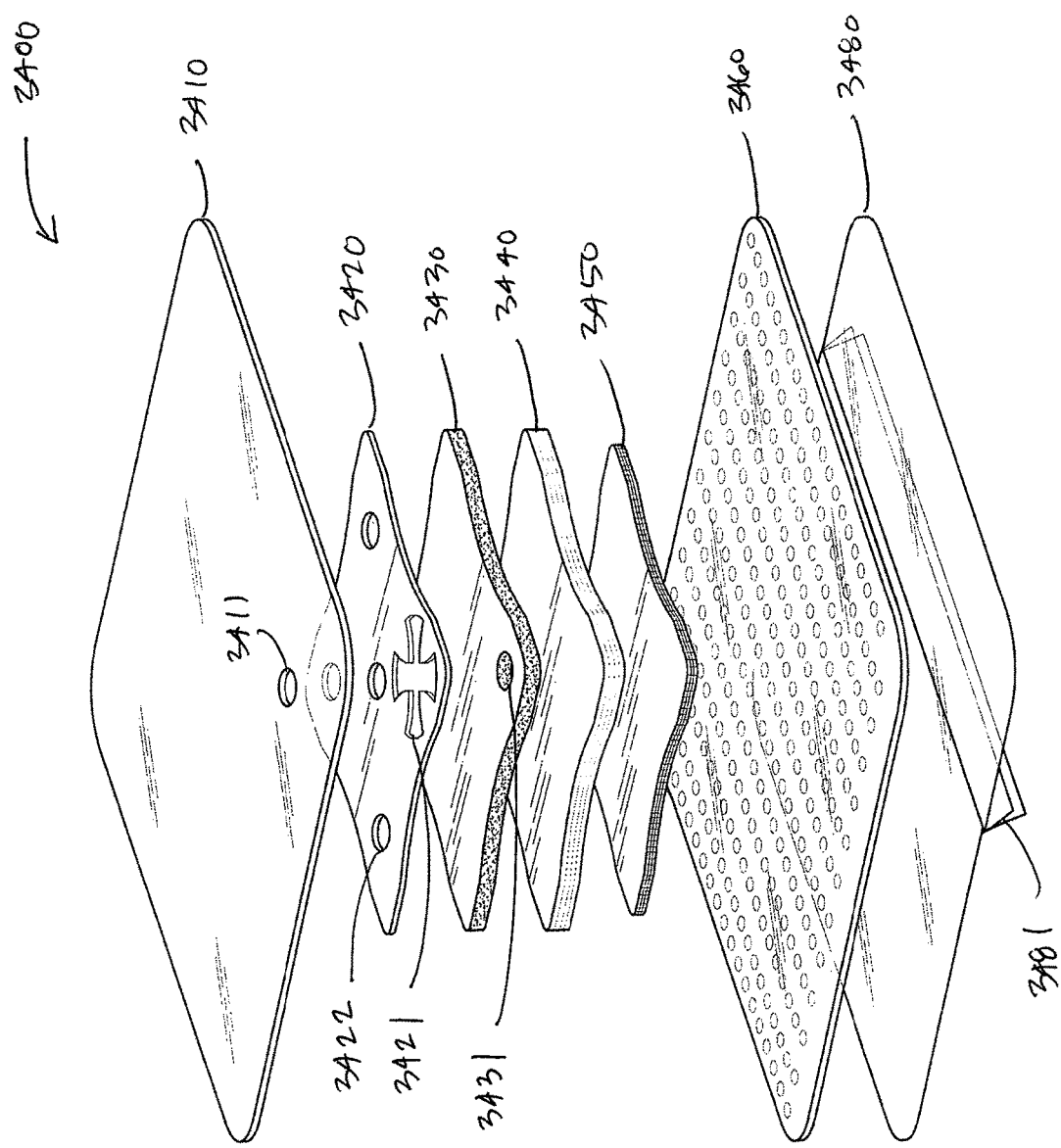
FIG. 4A illustrates an exploded view of an embodiment of a wound dressing.

FIG. 4A illustrates an exploded view of a dressing 3400 for use in negative pressure wound therapy. Although this figure illustrates a dressing having one particular shape, the construction of the layers can be applied to any of the embodiments identified below, including FIGS. 5A-8, and any of the dressing shapes and configurations described in the patent applications incorporated by reference herein. The dressing 3400 comprises a release layer 3480, wound contact layer 3460, a transmission layer 3450, an acquisition distribution layer 3440, an absorbent layer 3430, an obscuring layer 3420, and a backing layer 3410. The dressing 3400 may be connected to a port. At least the wound contact layer 3460, transmission layer 3450, absorbent layer 3430, obscuring layer 3420, and backing layer 3410 may have properties as described with respect to particular embodiments above, such as the embodiments of FIGS. 3A-C, as well as or instead of the properties described below.

The dressing 3400 may comprise a wound contact layer 3460 for sealing the dressing 3400 to the healthy skin of a patient surrounding a wound area. Certain embodiments of the wound contact layer may comprise three layers: a polyurethane film layer, a lower adhesive layer and an upper adhesive layer. The upper adhesive layer may assist in maintaining the integrity of the dressing 3400, and the lower adhesive layer may be employed for sealing the dressing 3400 to the healthy skin of a patient around a wound site. As described above, in some embodiments with respect to FIGS. 3A-C, some embodiments of the polyurethane film layer may be perforated. Some embodiments of the polyurethane film layer and upper and lower adhesive layers may be perforated together after the adhesive layers have been applied to the polyurethane film. In some embodiments a pressure sensitive adhesive, which may be a silicone, hot melt, hydrocolloid or acrylic based adhesive or other such adhesives, may be formed on both sides or optionally on a selected one side of the wound contact layer. In certain embodiments, the upper adhesive layer may comprise an acrylic pressure sensitive adhesive, and the lower adhesive layer may comprise a silicone pressure sensitive adhesive. In other embodiments the wound contact layer 3460 may not be provided with adhesive. In some embodiments, the wound contact layer 3460 may be transparent or translucent. The film layer of the wound contact layer 3460 may define a perimeter with a rectangular or a square shape. A release layer 3480 may be removably attached to the underside of the wound contact layer 3460, for example covering the lower adhesive layer, and may be peeled off using flaps 3481. Some embodiments of the release layer 3480 may have a plurality of flaps extending along the length of the layer 3480.

Some embodiments of the dressing 3400 may comprise an optional spacer or transmission layer 3450. The transmission layer 3450 may comprise a porous material or 3D fabric configured to allow for the passage of fluids therethrough away from the wound site and into the upper layers of the dressing 3400. In particular, the transmission layer 3450 can ensure that an open air channel can be maintained to communicate negative pressure over the wound area even when the absorbent layer 3430 has absorbed substantial amounts of exudates. The transmission layer 3450 should remain open under the typical pressures that will be applied during negative pressure wound therapy as described above, so that the whole wound site sees an equalized negative pressure.

Some embodiments of the transmission layer 3450 may be formed of a material having a three dimensional structure. For example, a knitted or woven spacer fabric (for example Baltex 7970 weft knitted polyester) or a non-woven fabric can be used. In some embodiments, the transmission layer 3450 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing 3400 where the absorbent layer 3430 helps lock the liquid away or itself wicks the liquid onwards towards the cover layer 3410 where it can be transpired. Other materials can be utilized, and examples of such materials are described in U.S. Patent Pub. No. 2011/0282309, which are hereby incorporated by reference and made part of this disclosure. However, the transmission layer 3450 may be optional, and for example may be optional in embodiments of the dressing 3400 which comprise the acquisition distribution layer 3440, described below.

Some embodiments may comprise a wicking or acquisition distribution layer (ADL) 3440 to horizontally wick fluid such as wound exudate as it is absorbed upward through the layers of the dressing 3400. Lateral wicking of fluid may allow maximum distribution of the fluid through the absorbent layer 3430 and may enable the absorbent layer 3430 to reach its full holding capacity. This may advantageously increase moisture vapor permeation and efficient delivery of negative pressure to the wound site. Some embodiments of the ADL 3440 may comprise viscose, polyester, polypropylene, cellulose, or a combination of some or all of these, and the material may be needle-punched. Some embodiments of the ADL 3440 may comprise polyethylene in the range of 40-150 grams per square meter (gsm).

The dressing 3400 may further comprise an absorbent or superabsorbent layer 3430. The absorbent layer can be manufactured from ALLEVYN™ foam, Freudenberg 114-224-4 and/or Chem-Posite™11C-450, or any other suitable material. In some embodiments, the absorbent layer 3430 can be a layer of non-woven cellulose fibers having superabsorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid.

For example, some embodiments of the absorbent layer 3430 may comprise a layered construction of an upper layer of non-woven cellulose fibers, superabsorbent particles (SAP), and a lower layer of cellulose fibers with 40-80% SAP. In some embodiments, the absorbent layer 3430 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer 3430 can have one or more through holes 3431 located so as to underlie the suction port.

Some embodiments of the present disclosure may optionally employ a masking or obscuring layer 3420 to help reduce the unsightly appearance of a dressing 3400 during use due to the absorption of wound exudate. The obscuring layer 3420 may be a colored portion of the absorbent material, or may be a separate layer that covers the absorbent material. The obscuring layer 3420 may be one of a variety of colors such as blue, orange, yellow, green, or any color suitable for masking the presence of wound exudate in the dressing 3400. For example, a blue obscuring layer 3420 may be a shade of blue similar to the shade of blue commonly used for the material of medical gowns, scrubs, and drapes. Some embodiments of the obscuring layer 3420 may comprise polypropylene spunbond material. Further, some embodiments of the obscuring layer 3420 may comprise a hydrophobic additive or coating. Other embodiments may comprise a thin fibrous sheet of 60, 70, or 80 gsm.

The obscuring layer may comprise at least one viewing window 3422 configured to allow a visual determination of the saturation level of the absorbent layer. The at least one viewing window 3422 may comprise at least one aperture made through the obscuring layer. The at least one viewing window 3422 may comprise at least one uncolored region of the obscuring layer. Some embodiments of the obscuring layer may comprise a plurality of viewing windows or an array of viewing windows.

The masking capabilities of the obscuring layer 3420 should preferably only be partial, to allow clinicians to access the information they require by observing the spread of exudate across the dressing surface. A obscuring layer 3420 may be partial due to material properties allowing wound exudate to slightly alter the appearance of the dressing or due to the presence of at least one viewing window 3422 in a completely obscuring material. The partial masking nature of the obscuring layer 3420 enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

The obscuring layer 3420 can have one or more through holes located so as to underlie the suction port. Some embodiments may have a maltese cross 3421 or other shaped cutout underlying the suction port, wherein the diameter of the maltese cross 3421 is greater than the diameter of the port. This may allow a clinician to easily assess the amount of wound exudate absorbed into the layers beneath the port.

The dressing 3400 may also comprise a backing layer, or cover layer 3410 extending across the width of the wound dressing. The cover layer 3410 may be gas impermeable but moisture vapor permeable. Some embodiments may employ a polyurethane film (for example, Elastollan SP9109) or any other suitable material. For example, certain embodiments may comprise translucent or transparent 30 gsm EU33 film. The cover layer 3410 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer 3410 can have an orifice 3411 located so as to underlie the suction port. The orifice 3411 may allow transmission of negative pressure through the cover layer 3410 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

Figure 4B:
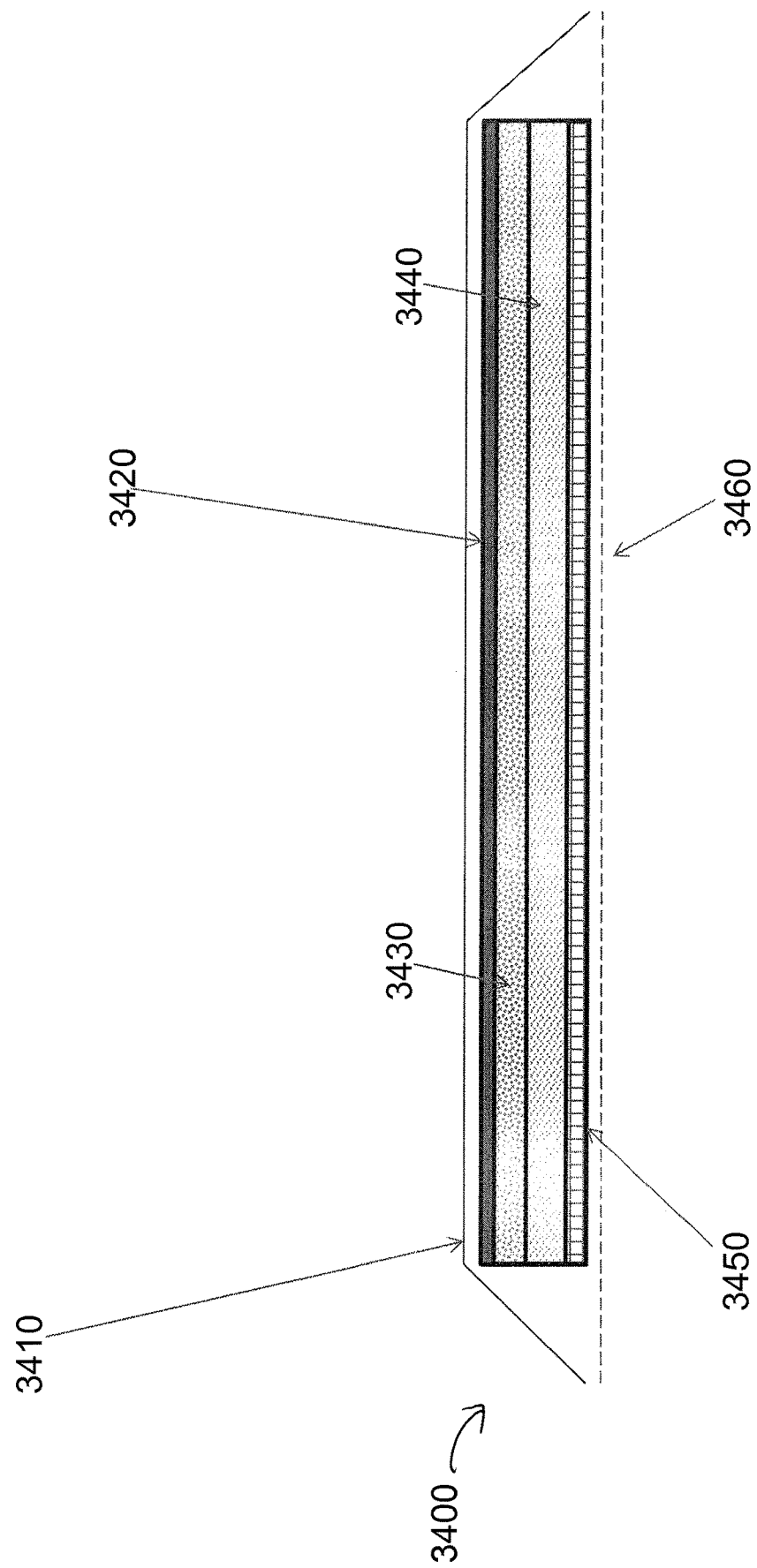
FIG. 4B illustrates a cross sectional view of an embodiment of a wound dressing.

FIG. 4B illustrates a cross sectional view of the wound dressing 3400, displaying an embodiment of the relative thicknesses of layers of the dressing 3400. In some embodiments, the wound contact layer 3460 may be flat and the top film layer 3410 may be contoured over the inner layers of the dressing 3400. The spacer layer 3450 may be half as thick as the acquisition distribution layer 3440 in some embodiments. In some embodiments, the absorbent layer 3430 may be about 1.5 times thicker than the spacer layer 3450. The obscuring layer 3420 may be about half the thickness of the spacer layer 3450.

Figure 5A:
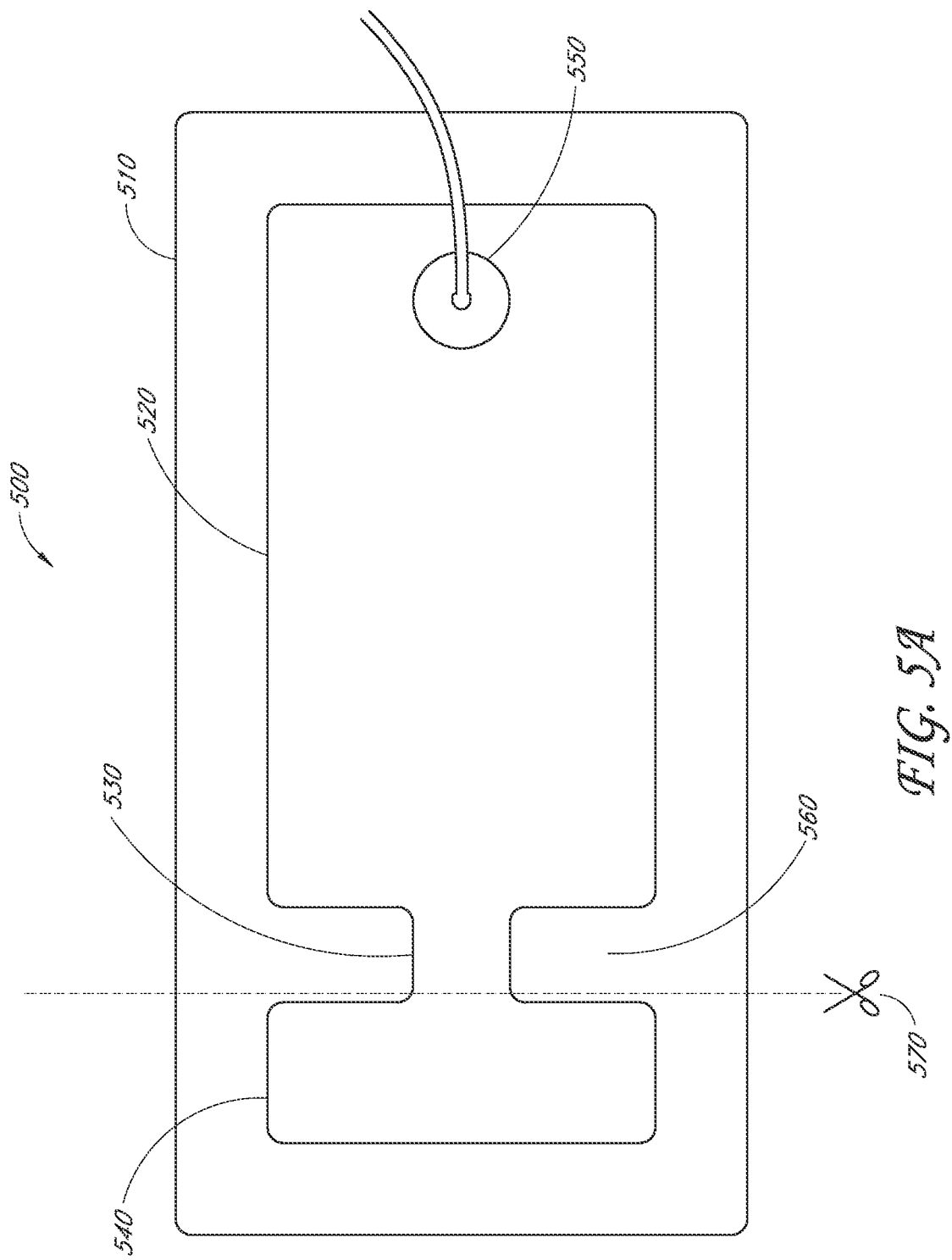
FIG. 5A illustrates an embodiment of a wound dressing trimmable at a bridge portion.
Figure 5B:
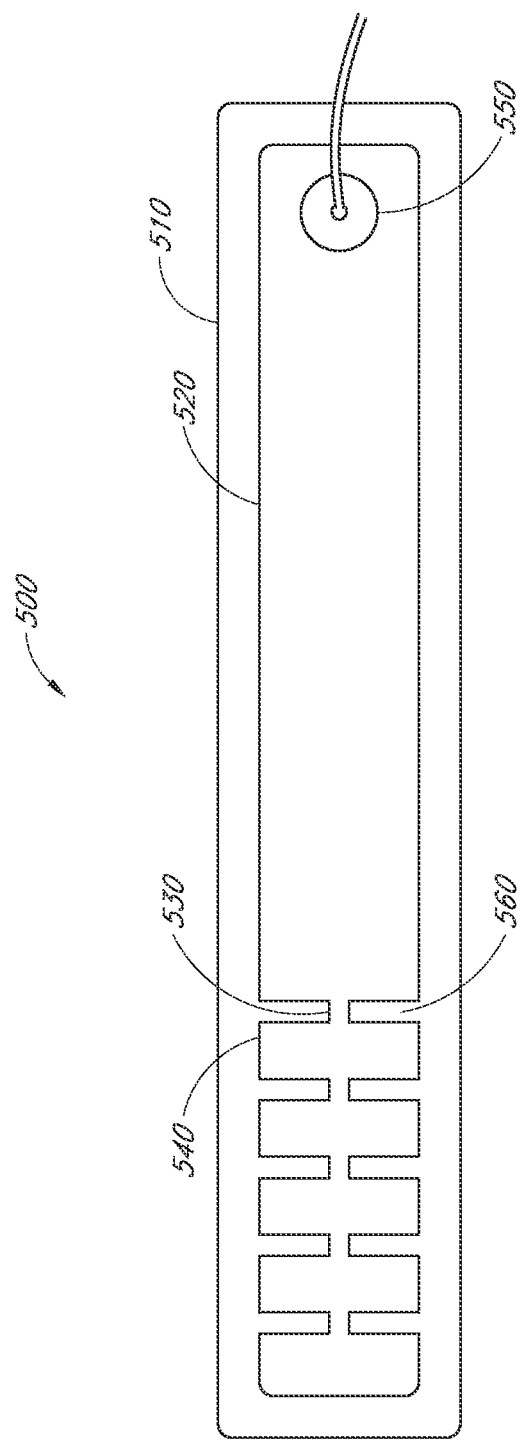
FIG. 5B illustrates another embodiment of a wound dressing trimmable at a bridge portion.

FIGS. 5A and 5B illustrate various embodiments of a wound dressing 500 which may be trimmable at a bridge portion 530. The dressing 500 may comprise a backing layer 510, an absorbent layer formed in a main portion 520 and at least one additional portion 540 separated by a gap 560 and connected by a bridge portion 530, and a port 550. As illustrated, the dressing has an elongate, rectangular shape, though other shapes are also contemplated. The absorbent layer preferably has a smaller footprint than the backing layer, so that the absorbent layer is completely surrounded by the backing layer. It will be appreciated that in some embodiments, the absorbent layer is an integral, one-piece layer of material that extends across the main portion 520, the additional portion 540 and in the bridge portion 530. Some embodiments may be manufactured without the port 550 and may include at least one area for attaching a port. For example, the port 550 may simply be an opening in the backing layer for attaching a separate port member.

The dressing 500 may also comprise other layers as discussed above with respect to FIGS. 3A-4B. For instance, the dressing 500 may comprise a wound contact layer which may be sealed to the backing layer 510, thereby creating an enclosed chamber for the absorbent layer and any other layers within the dressing. The wound contact layer and backing layer may be sealed along a perimeter with a certain distance from the edge of the sealed perimeter to the edge of the absorbent layer. The wound contact layer and backing layer may also be sealed together throughout some or all of the area of a gap 560 between portions of the inner layers.

Some embodiments of the dressing 500 may comprise a transmission or wicking layer, as described above, for the transmission of negative pressure throughout the dressing and for drawing wound exudate away from the wound site and into the upper layers of the dressing 500. Some embodiments may comprise an acquisition distribution layer for lateral transmission of fluids such as wound exudate. Some embodiments may employ both of these additional layers. Use of one or more of these layers may advantageously maintain fluid transmission through narrow portions of the dressing such as the bridge portions, and may keep these narrow portions from partially or completely collapsing under negative pressure.

As illustrated in FIG. 5B, the absorbent layer may comprise a main portion 520 and a plurality of additional portions 540. The additional portions may be smaller than or the same size as the main portion 550. For example, as measured along the longitudinal length of a rectangular dressing, the length of the additional portions may be smaller than the length of the main portion, and each additional portion may have the same length. As illustrated, the main portion 520 is connected to the first additional portion 540 by one bridge portion 530 aligned along the center longitudinal axis of the dressing 500, and each additional portion is connected to the next additional portion by a similar bridge. The bridge portion may in FIGS. 5A and 5B may also be located off the center axis, for example at the side of the dressing. Other embodiments may employ a plurality of bridges for connecting the portions of the dressing. For example, one embodiment may employ two bridges to connect adjacent portions, wherein the bridges are located at the side edges of the adjacent portions next to the sealed perimeter. Another embodiment may employ two bridges each located a distance away from the side edges of the adjacent portions.

In some embodiments the main portion 520 may be a precalculated minimum length, and some or all of the additional portions 540 may have lengths that can be removed for custom sizing of the dressing to a variety of lengths exceeding the minimum length. The main portion length may be longer than the additional portion lengths, or the main portion may have the same length as the additional portions. Such embodiments may be advantageous for a long incision such as a leg incision made for a vein harvest. In an embodiment, the main portion 520 may be a minimum incision length or minimum leg length, and the additional portions 540 may be included in the dressing to achieve a length up to a maximum incision length or a maximum leg length. In use, the dressing may be trimmed according to the incision or leg length of the patient across the bridge portions, for example at cut line 570 described below. In some embodiments, additional ports or port attachment sites may be located on some or all of the additional portions in order to maintain a substantially even level of negative pressure throughout a relatively long dressing.

The bridge portion 530 in FIGS. 5A and 5B creates a continuous path for negative pressure delivery between multiple portions of the dressing. The bridge portion 530 may have a width that is less than ⅛, ¼, or ⅓ the width of adjacent portions of absorbent material. A wider bridge portion allows for greater transmission of negative pressure and fluids such as wound exudate, however a narrower bridge portion is advantageous for sealing a dressing trimmed at the bridge portion. Further, patient comfort may be enhanced if the bridge portion 530 is wide enough to cover a wound or an incision. Embodiments of the dressings described herein may balance these factors according to a variety of purposes and/or considerations, and therefore the width of bridge portion 530 may vary. In some embodiments the bridge portion 530 may be approximately 15 mm wide, however other embodiments may be 10 mm to 20 mm (or about 10 mm to about 20 mm) wide or thinner or thicker. In embodiments employing a plurality of bridge portions, the bridge portions may all be a uniform width or may have varying widths.

In a dressing applied to a nonplanar surface, the bridge portions may also advantageously provide enhanced flexing of the dressing for conforming to the nonplanar surface. Further, the bridge portions may enhance side flexing capabilities of the dressing for covering a curved or arcuate incision. In some embodiments, the location and width of the bridge portions may be selected for both connecting a plurality of trimmable portions as well as for flexibility of the dressing.

The dressing 500 may be trimmed at or across the bridge portion 530. Although the dressing may be trimmed at any portion, trimming the dressing at bridge portion 530, for example perpendicular to the length of the dressing, enables easier sealing as a narrower cross sectional area is exposed, and thus less area requires sealing after trimming. In some embodiments, the gap 560 may have the same width as the distance from the sealed perimeter edge to the absorbent layer, such that when the dressing is trimmed along a trim line 570 adjacent to the additional portion 540 the sealed perimeter around the inner layer(s) is substantially unchanged. In some embodiments this width may be approximately 2.5 cm, and in other embodiments may be any width suitable for maintaining the seal between the backing layer and the wound contact layer. It will be appreciated that the dressing may be trimmed at locations other than the illustrated trim line 570, which is included for illustrative purposes only, for example at a trim line in the center of the bridge portion 530 or at a diagonal or curved trim line.

In some embodiments, the absorbent layer and/or other layers of the wound dressing may be prescored for sizing. Other layers, such as the transmission layer or acquisition distribution layer, may also be prescored. The backing layer may not be scored, as a through hole may limit the ability of the backing layer to function as a bacterial barrier or compromise the ability of the dressing to maintain negative pressure. Other embodiments may include a printed or indented pattern on some or all of the layers to indicate possible trim lines.

After trimming, the dressing 500 may be sealed by an adhesive strip, a piece of a sealing drape, by another dressing, or by a sealant. In some embodiments, a retention strip may be applied at the interface of the dressing edge and the skin. The retention strips may be applied to cover trimmed dressing borders. In some embodiments the retention strips may comprise a pressure-sensitive adhesive on the lower surface, and in other embodiments may be applied over a sealant. It will be appreciated that any other adhesive method or mechanism may be used to seal the dressing. For example, a sealant may be applied with a tool such as a syringe around the trimmed area in order to reseal the chamber of the dressing or to seal the dressing to a patient. Some embodiments of the dressing may be self-sealing.

Figure 6:
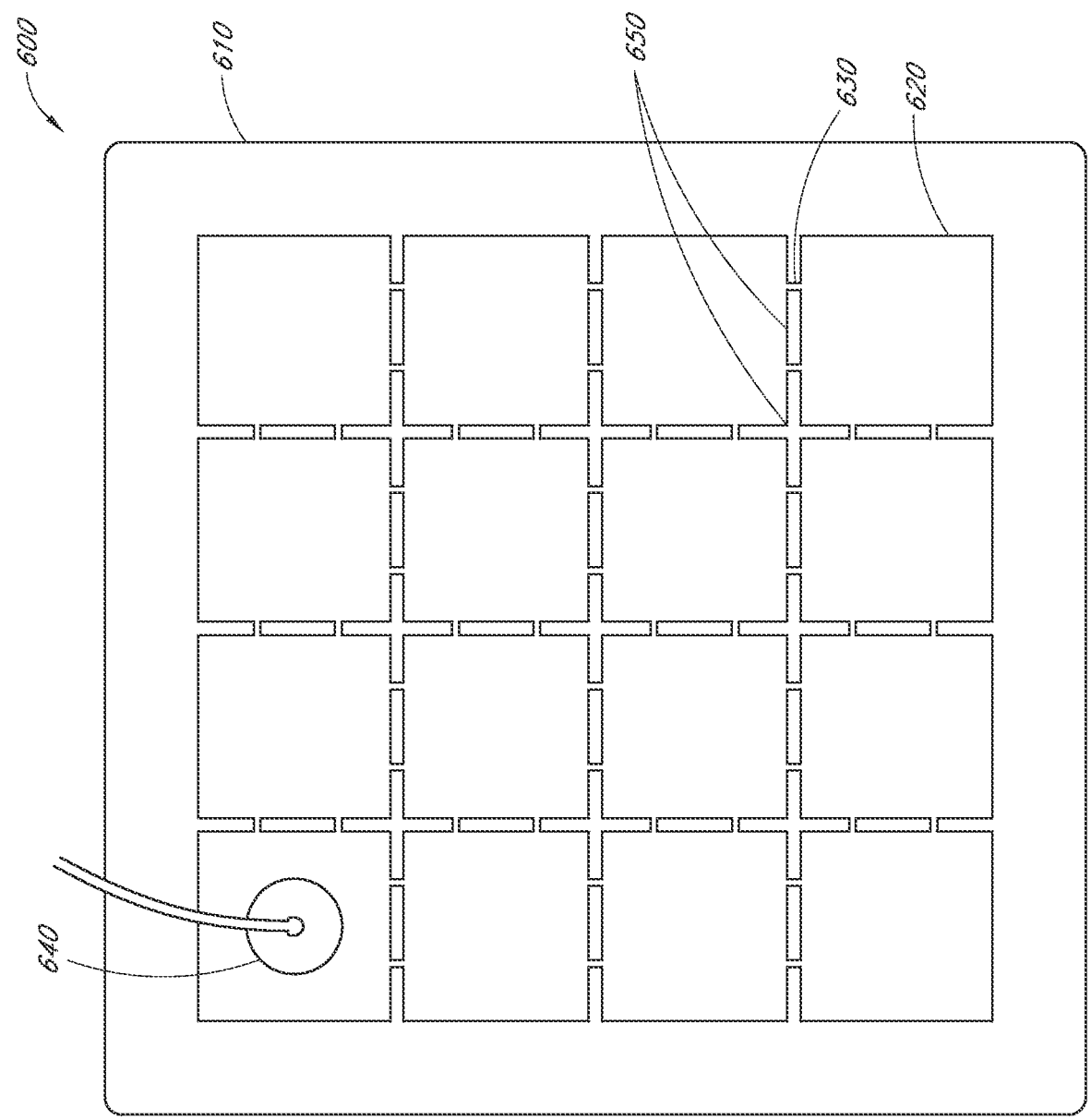
FIG. 6 illustrates an embodiment of a trimmable wound dressing comprising a plurality of portions or cells.

FIG. 6 illustrates an embodiment of a trimmable wound dressing 600 comprising a plurality of portions or cells 620. The dressing 600 may comprise a sealed perimeter 610 of a backing layer and a wound contact layer, a plurality of cells 620, a plurality of bridges 630 connecting adjacent portions, and a port member 640. As described above, the dressing 600 may be trimmed at the bridge portions and sealed along the trim line. Each of the cells 620 and bridge portions 630 may include absorbent material as described above, along with other optional layers.

As illustrated, the dressing comprises a 4×4 array of cells 620. Other embodiments may comprise any suitable array of cells, or may be configured as a long rolled dressing N cells wide. The cells may be connected by one or more narrow bridge portions 630 and separated by gaps 650. The backing layer and wound contact layer may be sealed together throughout the gaps. By trimming at the bridge portions 630, the integrity of the dressing may be maintained even as the dressing is significantly resized. For example, the dressing may be trimmed so that only one inner cell or a group of inner cells remain, and the layers of the dressing will not separate due to the sealing of the backing layer and wound contact layer throughout the area of the gaps 650.

In some embodiments, the center cells of the dressing 600 may be removed. This may provide benefits, for example, when the dressing is used to cover a grafted skin flap or sutured skin flap. The dressing may be resized so that the unsutured skin is substantially uncovered by the dressing. Thus, the removed sections would otherwise cover the healthy skin of the flap. Covering the healthy skin with the dressing potentially creates problem such as exposing the wound to bacteria on the surface of the flap and exposing the healthy skin of the flap to excess moisture. The dressing may also be resized accordingly to cover circular, curved, or otherwise irregularly shaped suture lines.

The port member 640 may be located, as illustrated, on a corner cell of the dressing 600. However, in other embodiments the port may be located on a different cell. Some embodiments may employ multiple ports, each port connected to a different cell. For example, a large dressing or longed rolled dressing may comprise a port at an edge cell of every N rows, such every as four rows or five rows. Some embodiments may, instead of the illustrated port member 640, comprise a port attachment site or sites.

Figure 7:
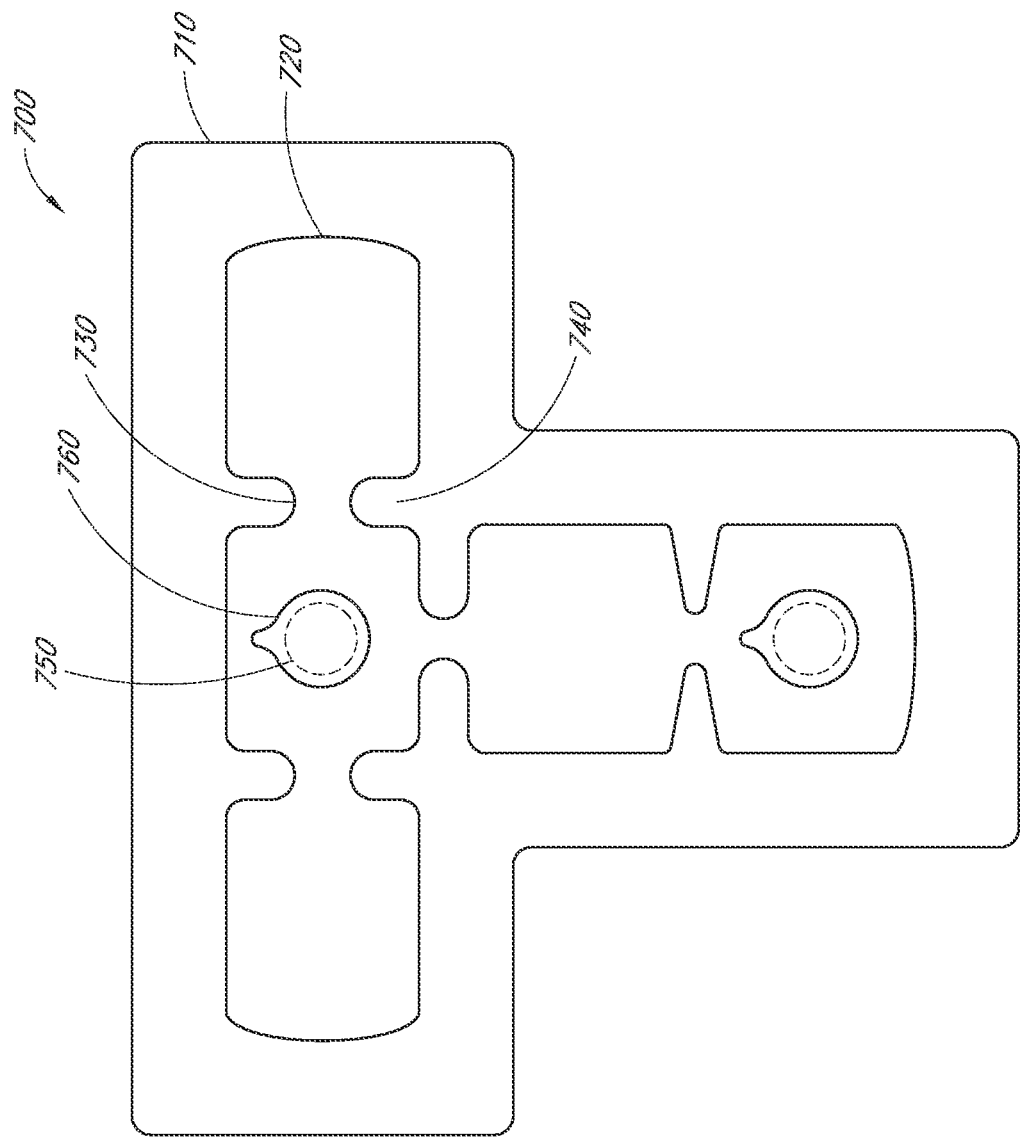
FIG. 7 illustrates an embodiment of a trimmable T-shaped wound dressing comprising a plurality of portions with multiple port attachment sites.

FIG. 7 illustrates an embodiment of a trimmable wound dressing 700 comprising a plurality of portions with multiple port attachment sites 760. Similar to the dressing 600 described above, the T-shaped dressing 700 comprises a backing layer and wound contact layer having a sealed perimeter 710 around a plurality of cells 720 containing absorbent material connected by bridge portions 730 and separated by gaps 740. The backing layer and wound contact layer may also be sealed together throughout some or all of the area of the gaps 740. As described above, the dressing 700 may be trimmed at the bridge portions and sealed along the trim line. Although the dressing is illustrated as being T-shaped, this is for illustrative purposes only, and the dressing may be a variety of branched shapes. Each branch may comprise one or more cells connected by one or more bridge portions.

The dressing comprises a plurality of port attachment sites 760. Each attachment site 760 may be a hole in the backing layer and may be covered with a removable tab 760. The tab may comprise a suitable backing material with a layer of adhesive on some or all of the lower surface. Some embodiments may comprise a ring of adhesive sized to surround the hole 750 in the backing layer. The tab 760 may be removed so that a port may be attached to the backing layer over the hole 750 for transmission of negative pressure into the dressing 700. In some embodiments, port attachments may be secured at just one port attachment site. In other embodiments, port attachments may be secured over a plurality of attachment sites as needed for transmission of negative pressure throughout the dressing. Some ports may comprise an adhesive on the lower surface thereof for attachment to the dressing. Some embodiments of the dressing may comprise an adhesive layer for attaching the port.

Figure 8:
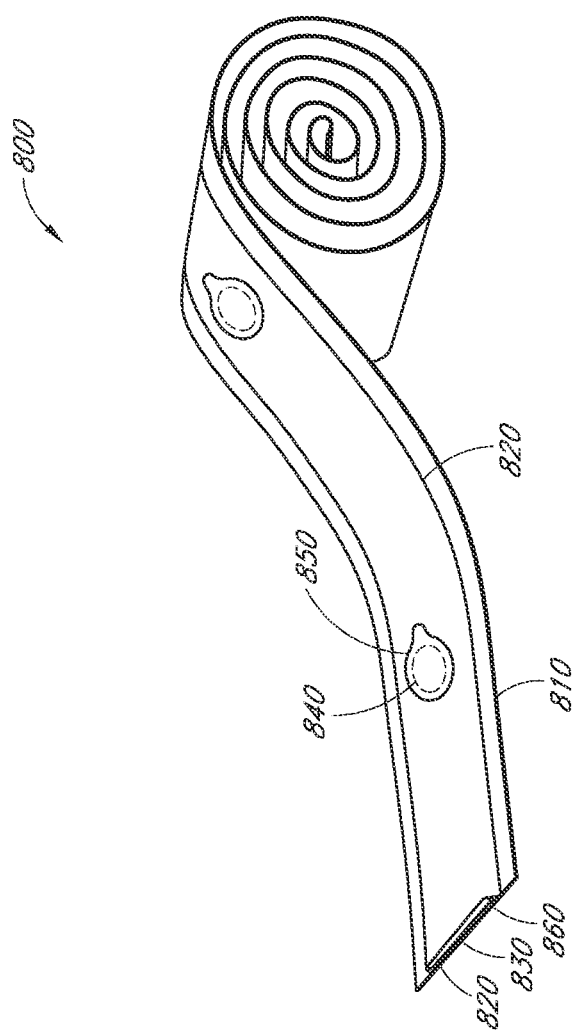
FIG. 8 illustrates an embodiment of a trimmable wound dressing with multiple port attachment sites.

FIG. 8 illustrates an embodiment of a trimmable wound dressing 800 with multiple port attachment sites 840. The dressing comprises a backing layer and wound contact layer having a sealed perimeter 710, an absorbent layer 820, an optional spacer layer 830 below the absorbent layer, and a plurality of holes 840 in the backing layer covered by tabs 850. The spacer layer 830 may be one or both of the transmission layer and acquisition distribution layer discussed above.

The dressing 800 is configured as a roll with port attachment sites 840 spaced a distance apart along the upper surface. In some embodiments this distance may be uniform between all port attachment sites, and in other embodiments the distance may vary. The dressing roll may be custom sized by unrolling a length of dressing, trimming the dressing, sealing the two sides, and attaching a port or ports to one or more port attachment sites. In some embodiments, unused port attachment sites 840 may remain sealed by adhesive tabs 850. In some embodiments, the absorbent layer 820 may comprise a bridge portion or plurality of bridge portions located between each port attachment site for ease of sealing a trimmed dressing. It will be appreciated that any of the dressings described above may be configured as a trimmable roll with a plurality of port attachment sites located a distance apart on the roll. For example, an elongate dressing configured as a roll may include narrower bridging portions spaced along a length of the dressing between port attachment sites to facilitate trimming of the dressing to a suitable size.

Such adaptable, resizable dressings may provide the advantage of reducing the inventory of dressings that a hospital or clinic is required to keep. Rather than maintaining a large inventory of dressings consisting of a multitude of shapes and sizes for all possible wound or incision sites, a hospital or clinic may only require one or several of the dressings described herein which can be modified to suit any patient needs. Further, it may be advantageous from a manufacturing perspective to produce adaptable dressings.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus for treatment of a wound site comprising a wound dressing comprising a length and a width configured to extend across the wound site, the wound dressing further comprising:

a backing layer having an upper surface and a lower surface and defining a perimeter configured to be positioned over skin surrounding the wound site;

a wound contact layer;

a plurality of cells each comprising an absorbent material positioned between the backing layer and the wound contact layer;

one or more bridging portions comprising:

a gap region of the backing layer and wound contact layer separating adjacent cells of the plurality of cells, wherein the backing layer and the wound contact layer are sealed throughout the gap region, and wherein a width of the backing layer and a width of the wound contact layer along the width of the wound dressing remain constant across each bridging portion and the adjacent cells, and a material layer positioned between the backing layer and the wound contact layer and connecting adjacent cells of the plurality of cells, the material layer of each bridging portion having a width along the width of the wound dressing smaller than ⅓ of a width of the absorbent material of the adjacent cells along the width of the wound dressing, the material layer configured to transmit negative pressure and fluid through the smaller width of the material layer at the one or more bridging portions during application of topical negative pressure at the wound site, wherein the wound dressing is configured to have an exposed cross-section of the material layer and a sealed perimeter around the exposed portion of the material layer when the wound dressing is trimmed at the one or more bridging portions along the width of the wound dressing, such that the wound dressing can be sealed by sealing the exposed cross-section of the material layer; and a port configured to transmit negative pressure through the backing layer for the application of the topical negative pressure at the wound site.

2. The apparatus of claim 1, wherein the port comprises an opening in the backing layer.

3. The apparatus of claim 1, wherein the port comprises a port member attached to the backing layer over an opening in the backing layer.

4. The apparatus of claim 3, wherein the port member is sealed to the upper surface of the backing layer.

5. The apparatus of claim 1, wherein the wound dressing further comprises a transmission layer between the wound contact layer and the absorbent material in the main portion.

6. The apparatus of claim 1, wherein the wound dressing further comprises an acquisition distribution layer between the wound contact layer and the absorbent material in the main portion.

7. The apparatus of claim 1, wherein one of the plurality of cells comprises a main portion having a rectangular shape having a longitudinal axis extending along its length.

8. The apparatus claim 7, wherein one or more of the absorbent material, a transmission layer, and an acquisition distribution layer comprises the one or more bridging portions centered on the longitudinal axis.

9. The apparatus of claim 7, wherein one or more of absorbent material, a transmission layer, and an acquisition distribution layer comprises three or more bridging portions centered on the longitudinal axis.

10. The apparatus of claim 1, wherein the one or more bridging portions have a width that is less than ¼ of a width of adjacent portions of absorbent material.

11. The apparatus of claim 1, wherein the one or more bridging portions have a width that is less than ⅛ of a width of adjacent portions of absorbent material.

12. The apparatus of claim 1, wherein the main portion has a T-shape with at least one bridging portion on each leg of the T.

13. The apparatus of claim 1, wherein the wound treatment apparatus is rolled into a tape which can be cut along the one or more bridging portions.

14. A method of treating a wound site, comprising:

providing a wound dressing comprising a length and a width configured to extend across the wound site, the wound dressing further comprising:

a backing layer;

a wound contact layer;

a plurality of cells each comprising an absorbent material positioned between the backing layer and the wound contact layer; and one or more bridging portions comprising:

a gap region of the backing layer and wound contact layer separating adjacent cells of the plurality of cells, wherein the backing layer and the wound contact layer are sealed throughout the gap region, and wherein a width of the backing layer and a width of the wound contact layer along the width of the wound dressing remain constant across each bridging portion and the adjacent cells, and a material layer positioned between the backing layer and the wound contact layer and connecting adjacent cells of the plurality of cells, the material layer of each bridging portion having a width along the width of the wound dressing smaller than a width of the absorbent material of adjacent cells of the plurality of cells along the width of the wound dressing, the material layer configured to transmit negative pressure and fluid through the smaller width of the material layer at the one or more bridging portions during application of negative pressure to the wound;

removing a portion of the wound dressing along at least one bridging portion of the one or more bridging portions to create one or more exposed cross-sections of the material layer and a sealed perimeter on a remaining portion of the wound dressing at the at least one bridging portion;

positioning the remaining portion of the wound dressing over the wound;

sealing the remaining portion to skin surrounding the wound, wherein sealing comprises sealing the one or more exposed cross-sections of the material layer of the remaining portion; and applying the negative pressure to the wound through the backing layer of the remaining portion.

15. The method of claim 14, wherein removing the portion of the wound dressing comprises cutting the wound dressing across at least one of the one or more bridging portions.

16. The method of claim 14, wherein at least a portion of the wound dressing comprises pre-cut score marks to facilitate removing of the portion of wound dressing.

17. The method of claim 14, wherein the dressing comprises a plurality of openings in the backing layer covered with a releasable tab, and wherein negative pressure is applied to the backing layer through one of the openings.

18. The method of claim 14, wherein the dressing comprises a plurality of openings in the backing layer covered with a releasable tab, and wherein negative pressure is applied to the backing layer through two or more of the openings.

19. The method of claim 14, wherein the portion of the wound dressing is removed to size the remaining portion for positioning over an incisional wound.

20. The method of claim 14, wherein the portion of the wound dressing is removed to size the remaining portion for positioning over an elongate leg wound.

21. The method of claim 14, wherein the portion of the wound dressing is removed to size the remaining portion for positioning over an arcuate incisional wound.

22. The apparatus of claim 1, wherein at least one of the one or more bridging portions is connected at a first end to a main cell and at a second end to a secondary cell that is smaller than the main cell.

23. The apparatus of claim 1, wherein the material layer of the one or more bridging portions comprises an extension of the absorbent material of at least one of the plurality of cells.

24. The apparatus of claim 23, wherein the backing layer and the wound contact layer are sealed to each other to form the wound dressing containing the absorbent material there between, wherein the backing layer and the wound contact layer extend across the width of the wound dressing, and wherein widths of the backing layer and the wound contact layer are uniform across the plurality of cells and the one or more bridging portions, with the absorbent material at the one or more bridging portions having the smaller width than the absorbent material at the plurality of cells.

25. The apparatus of claim 1, wherein the perimeter of the backing layer is rectangular having a length extending along a longitudinal axis and having the width extending transverse to the longitudinal axis.

26. The method of claim 14, wherein the perimeter of the backing layer is rectangular having a length extending along a longitudinal axis and having the width extending transverse the longitudinal axis.

27. The apparatus of claim 1, wherein the material layer is constructed from a material different from the absorbent material.

28. The method of claim 14, wherein the material layer is constructed from a material different from the absorbent material.

* * * * *